US008992397B2

(12) United States Patent
Sato

(10) Patent No.: US 8,992,397 B2
(45) Date of Patent: Mar. 31, 2015

(54) MUSCLE TRAINING APPARATUS AND BELT FOR MUSCLE TRAINING

(75) Inventor: Yoshiaki Sato, Tokyo (JP)

(73) Assignee: Kaatsu Japan Co., Ltd., Tokyo (JP)

( * ) Notice: Subject to any disclaimer, the term of this patent is extended or adjusted under 35 U.S.C. 154(b) by 1335 days.

(21) Appl. No.: 12/674,839

(22) PCT Filed: Aug. 19, 2008

(86) PCT No.: PCT/JP2008/065062
§ 371 (c)(1),
(2), (4) Date: Feb. 9, 2011

(87) PCT Pub. No.: WO2009/028430
PCT Pub. Date: Mar. 5, 2009

(65) Prior Publication Data
US 2011/0160022 A1 Jun. 30, 2011

(30) Foreign Application Priority Data
Aug. 24, 2007 (JP) ................................ 2007-219113

(51) Int. Cl.
*A63B 21/008* (2006.01)
*A61F 13/00* (2006.01)
(Continued)

(52) U.S. Cl.
CPC .............. *A63B 23/12* (2013.01); *A61H 9/0078* (2013.01); *A61H 9/0092* (2013.01); *A61H 11/00* (2013.01);
(Continued)

(58) Field of Classification Search
CPC ................... A63B 21/00058; A63B 21/00069; A63B 21/008; A63B 21/0081; A63B 21/0085; A63B 21/14; A63B 21/1423; A63B 21/1426; A63B 21/1434; A63B 21/1442
USPC ............. 482/1–9, 91–92, 111–113, 131, 139, 482/148, 901; 601/23, 84, 148–152; 602/1, 602/13, 41, 61–65, 74; 606/202–203
See application file for complete search history.

(56) References Cited

U.S. PATENT DOCUMENTS 2,660,174 A * 11/1953 Saemann ..................... 606/202
4,948,117 A 8/1990 Burke
(Continued)

FOREIGN PATENT DOCUMENTS

EP 1652557 5/2006
JP 4718795 6/1972
(Continued)

*Primary Examiner* — Oren Ginsberg
(74) *Attorney, Agent, or Firm* — Edell, Shapiro & Finnan, LLC

(57) ABSTRACT

To ensure easy and secure placement of a belt for KAATSU muscle training on a target compressed site near the proximal portion of a limb.

A belt 100B has a longer first band-shaped member 110 and a shorter second band-shaped member 120 both of which have a band shape and are connected to a ring-shaped joint member 130 at their respective ends. In order to place the belt 100B on the target compressed site, the limb (right leg in this case) on which the belt 100B is expected to be placed is inserted into a loop of the first band-shaped member 110 formed by passing the end of the first band-shaped member 110 through an opening in the joint member 130, and the belt is moved up to the target compressed site. Then, the first band-shaped member 110 and the second band-shaped member 120 are pulled with both hands in the opposite directions. The belt 100B is placed on the target compressed site with the belt 100B being tensioned appropriately.

9 Claims, 12 Drawing Sheets

100B

(51) Int. Cl.

| | |
|---|---|
| ***A61F 13/06*** | (2006.01) |
| ***A61F 15/00*** | (2006.01) |
| ***A63B 23/12*** | (2006.01) |
| ***A61H 9/00*** | (2006.01) |
| ***A61H 11/00*** | (2006.01) |
| ***A63B 21/00*** | (2006.01) |

(52) U.S. Cl.
CPC ......... *A63B 21/0085* (2013.01); *A63B 21/1434* (2013.01); *A63B 21/1449* (2013.01); *A61H 2201/5038* (2013.01); *A61H 2201/5071* (2013.01); *A61H 2205/06* (2013.01); *A61H 2205/10* (2013.01); *A63B 2213/006* (2013.01); *A63B 2220/56* (2013.01)
USPC ............................................. 482/111; 602/62

(56) References Cited

U.S. PATENT DOCUMENTS

| | | | | |
|---|---|---|---|---|
| 4,963,410 | A * | 10/1990 | Bryant | 428/100 |
| 6,149,618 | A * | 11/2000 | Sato | 602/75 |
| 6,317,933 | B1 * | 11/2001 | Suenaga | 24/16 R |
| 7,384,379 | B2 * | 6/2008 | Egger | 482/78 |
| 2006/0128538 | A1 * | 6/2006 | Sato et al. | 482/112 |
| 2006/0142128 | A1 * | 6/2006 | Sato | 482/112 |
| 2006/0281611 | A1 | 12/2006 | Sato | |

FOREIGN PATENT DOCUMENTS

| | | | |
|---|---|---|---|
| JP | 7144027 | A | 6/1995 |
| JP | 10085361 | A | 4/1998 |
| JP | 10085362 | A | 4/1998 |
| JP | 2001214304 | A | 8/2001 |
| JP | 2004215858 | A | 8/2004 |
| JP | 2004313423 | A | 11/2004 |
| JP | 2005000509 | A | 1/2005 |
| JP | 2005006921 | A | 1/2005 |
| JP | 2005-065874 | | 3/2005 |
| JP | 2005058544 | A | 3/2005 |
| JP | 2006218058 | A | 8/2006 |
| JP | 2007125254 | A | 5/2007 |
| KR | 10-2006-0052704 | | 5/2006 |
| WO | 2006-097739 | | 9/2006 |

* cited by examiner

MUSCLE TRAINING APPARATUS AND BELT FOR MUSCLE TRAINING

TECHNICAL FIELD

The present invention relates to a training apparatus for the muscle development. More particularly, the present invention relates to a KAATSU muscle training apparatus suitable for KAATSU muscle training that allows healthy people having no motor abnormalities as well as people having motor abnormalities to develop their muscles in an effective manner, and to a belt for such KAATSU muscle training.

BACKGROUND OF THE INVENTION

Dr. Yoshiaki Sato, the present inventor, has conducted researches and investigations for a long time in order to develop a muscle strength increasing method for easy, safe, and effective muscle development, and put together the accomplishments into a patent application having Japanese Patent Application No. 5-313949, which has been granted as Japanese Patent No. 2670421. In addition, the present inventor filed a U.S. patent application claiming priority of this application, which has been granted as U.S. Pat. No. 6,149,618.

In addition, the present inventor has gone over about the KAATSU muscle training on a daily basis, and invented some inventions for devices and apparatuses for use in implementing a KAATSU muscle training method, as disclosed in Japanese Patent Laid-Open Nos. 10-85361, 10-85362, 2004-215858, 2004-313423, 2005-509, and 2005-6921.

The muscle training method described in these applications is spreading fast in Japan because of its beneficial effects as described below. In addition, national and foreign physicians as well as universities have made researches and investigations about it and, as a result of them researchers including the present inventor have published many articles.

The muscle strength increasing method according to these patents is a distinctive non-conventional one that involves compression of an armor leg at a position near the top thereof. This muscle strength increasing method (the subject muscle strength increasing method is herein referred to as a "KAATSU muscle training method"; the present applicant is active in promoting the KAATSU muscle training method under the name of a KAATSU training method, and the related trade names such as "KAATSU training", "KAATSU TRAINING", and"KAATSU" are trademarks claimed by the applicant of the present invention) is based on the following theoretical concept.

Muscles are composed of slow-twitch muscle fibers and fast-twitch muscle fibers. Slow-twitch muscle fibers are limited in their potential for growth. Accordingly, it is necessary to recruit fast-twitch muscle fibers of the slow- and fast-twitch muscle fibers in order to develop muscles. Recruitment of fast-twitch muscle fibers causes lactic acid buildup in the muscles, which triggers secretion of growth hormone from the pituitary. The growth hormone has effects of, for example, promoting muscle growth and shedding body fat. This means that recruitment and exhaustion of fast-twitch muscle fibers results in development of fast-twitch muscle fibers and, in turn, the entire muscles.

Slow-twitch muscle fibers and fast-twitch muscle fibers are different from each other in terms of the following. Slow-twitch muscle fibers use oxygen for energy and are recruited for low-intensity activities. Fast-twitch muscle fibers provide for activities regardless of whether or not oxygen is present. They are recruited after the slow-twitch muscle fibers for highly intense activities. Therefore, it is necessary to cause the earlier recruited and activated slow-twitch muscle fibers to be exhausted soon in order to recruit fast-twitch muscle fibers.

Conventional muscle strength increasing methods use heavy exercises with, for example, a barbell to cause the slow-twitch muscle fibers to be exhausted first, and then to recruit the fast-twitch muscle fibers. This recruitment of fast-twitch muscle fibers requires a significant amount of exercises, is time-consuming, and tends to increase the burden on muscles and joints.

On the other hand, muscle exercise may be performed under the restriction of muscle blood flow into the limb distal to a predetermined position by means of applying pressure upon the muscles at the predetermined position near the top of the limb. Since less oxygen is supplied to these muscles, the slow-twitch muscle fibers, which require oxygen for energy, are thus exhausted in a short period of time. Muscle exercises with blood-flow restriction by application of pressure will result in recruitment of the fast-twitch muscle fibers without needing a large amount of exercises. More specifically, when pressure is applied circumferentially upon a limb at a predetermined position near the top of the limb, venous circulation is restricted while arterial circulation is kept almost the same as the normal condition if an appropriate pressure is applied. This is because veins are closer to the skin surface of the limb, and are thinner and less muscular (less resistant against an force for pressurization) than arteries while arteries are found deep within the limb, and are thicker and more muscular than veins. By holding that condition for a certain period of time, the limb that has compressed near the top thereof becomes engorged with blood which runs from arteries but cannot flow through veins. This promotes a state of blood pooling in the capillaries where such an amount of blood is not flowing normally. The limb that is compressed at a position near the top thereof gets into a state as if it were doing heavy exercises. During this time, because of the temporal occlusion of the veins, the muscle fatigue is caused by the fact that the lactic acid that has built up in the muscles is less likely to be removed from the muscles. Furthermore, the brain receives information of strenuous exercise from muscles, and brain's physiological action is then responsible for the production of a much more growth hormone than is usually produced during the daily life for muscle regeneration as well as during typical exercises.

In other words, the KAATSU muscle training method contributes to artificially produce a state which otherwise will occur during and after heavy exercises. It is possible to cause muscle fatigue much more heavily than would be produced normally with that amount of exercises. In addition, the user can "trick" the brain into secreting a larger amount of growth hormone.

Because of the aforementioned mechanism, restriction of muscle blood flow can allow users to significantly develop their muscles.

The KAATSU muscle training method is premised on the theoretical concept of the muscle strength increase by the restriction of blood flow. More specifically, the KAATSU muscle training method involves the application of an appropriate force for pressurization to at least one of the limbs at a predetermined position near the top thereof to restrict the blood flow restriction into the limb distal to that position. The force for pressurization serves to put an appropriate stress attributed to blood flow decrease on the muscles. Thus, the muscles can be developed in an effective manner.

The KAATSU muscle training method features muscle development without any exercises because it involves developing muscles by putting a stress attributed to blood flow decrease on the muscles. With this feature, the KAATSU muscle training method is highly effective for the recovery of motor ability in people with impaired motor function, e.g., the elders or an injured person.

In addition, the KAATSU muscle training method can compensate for a total amount of stress that is placed on the muscles by putting on the muscles a stress attributed to blood flow decrease. When combined with some exercises, the method advantageously reduces an exercise-related load as compared with conventional methods. This feature produces effects of reducing possible risks of joint- or muscle-damages and shortening a necessary time period for training, because it can decrease the amount of muscle exercises for the muscle development.

It should be noted that, for the implementation of the KAATSU muscle training method, such a device or apparatus is essential that can restrict the blood flow through the muscles that are subject to be developed and that can precisely adjust the degree of blood flow restriction.

The present inventor has gone over about such devices and apparatuses.

A belt for the KAATSU muscle training that the present inventor suggested was, for example, as disclosed in Japanese Patent Application No. 5-313949. The belt comprises a band-shaped member having a band shape, and loop fastening means (e.g., a hook-and-loop fastener) for use in maintaining the diameter of a loop of the strop-shaped member that is formed into the loop when wrapped around the proximal portion of an arm or leg.

In addition, the present inventor invented a KAATSU muscle training apparatus described in Japanese Patent Laid-Open No. 2005-58544. A belt for the KAATSU muscle training in the subject invention comprises a band-shaped member having a band- or tube-like shape, and loop fastening means as in the case described above. Besides, an air-tight inflatable pneumatic bag is provided on the inner surface (the surface to be in contact with an arm or leg when the band-shaped member is wrapped around the arm or leg) of the band-shaped member if the band-shaped member has a band shape or inside the band-shaped member if the band-shaped member has a tube-like shape. The belt for the KAATSU muscle training is connected to an inflatable pneumatic bag via a predetermined tube through which the inflatable pneumatic bag is supplied with air. In addition, the belt is used in combination with a device having a pump for removing the air from the inflatable pneumatic bag. This device controls the air pressure within the inflatable pneumatic bag and, in turn, adjusts appropriately the force to compress the limb.

The belt for the KAATSU muscle training of the former type that has no inflatable pneumatic bag is simple in structure and is advantageous in economic considerations because it requires no device having a pump as described above. In addition, this belt has an advantage of being easy to use, and thus being less likely to disturb exercises for the KAATSU muscle training by a person who receives the KAATSU muscle training.

On the other hand, the belt for the KAATSU muscle training of the latter type that has an inflatable pneumatic bag has a rather complex structure as compared with the belt of the former type. However, it has an advantage of being able to provide easier and safer KAATSU muscle training because the control by the aforementioned device having a pump allows appropriate adjustment of a compression force to be applied to the limb of a person who receives the KAATSU muscle training. In addition, the belt of the latter type has another advantage of being able to vary the compression force that the belt is applying to the proximal portion of the limb by means of changing the air pressure within the inflatable pneumatic bag, even during the KAATSU muscle training.

The belt having the inflatable pneumatic bag and the belt having no inflatable pneumatic bag are both useful and both are actually commercialized, despite the fact that their functions may be suitable in some cases or unsuitable in other cases, depending on the final use.

However, such a belt for the KAATSU muscle training still has a point that should be improved.

Both of the belt having the inflatable pneumatic bag and the belt having no inflatable pneumatic bag often adopt one of the following two structures: one is of a straight type, and the other is of a folded-back type.

They are described one by one.

A belt of the straight type is shown in FIG. 11. What is shown in FIG. 11 is a cross-sectional view in longitudinal direction of a belt of the straight type having an inflatable pneumatic bag therein.

This belt comprises a band-shaped member "a" that is made of stretchable fabric into an end-closed tube-like shape, and an elongated air-tight inflatable pneumatic bag "b", as shown in FIGS. 11(A) to 11(C). The inflatable pneumatic bag "b" is housed within the band-shaped member "a" so that one end thereof is aligned with one end of the band-shaped member "a". The inflatable pneumatic bag "b" is shorter than the band-shaped member "a". Accordingly, the other end of the inflatable pneumatic bag "b" does not reach the other end of the band-shaped member "a".

This belt is wrapped around a proximal portion of an arm or leg of a person who receives the KAATSU muscle training, as shown in FIGS. 11(B) and 11(C). The symbol "L" in FIGS. 11(B) and 11(C) represents a cross section of an arm of a person who receives the KAATSU muscle training.

As shown in FIG. 11(B), when the belt is wrapped around the arm, one end of the band-shaped member "a" is in contact with a predetermined position on the arm, and the other end thereof comes full circle (or more when the belt is longer) around the arm "L".

Then, in the state shown in FIG. 11(C), the other end of the band-shaped member "a" is pulled in the direction depicted by the arrow in FIG. 11(C) to apply predetermined tension. Thus, the belt is tightened around the arm. An appropriate compression force is applied to the proximal portion of the arm by means of supplying and removing air into and from the inflatable pneumatic bag "b" of the belt via a tube which is not shown but is connected to the inflatable pneumatic bag "b".

This belt has a disadvantage in that when a user tries to pull the other end of the band-shaped member "a" in the state shown in FIG. 11(C), the whole band-shaped member "a" rotates about the arm "L" (or leg) in the direction depicted by the arrow because one end of the band-shaped member "a" is not secured, which makes it difficult to appropriately tension the belt. This means that considerable skill is required to place the belt on an arm or leg while the belt is tensioned appropriately. In particular, the rotation as described above is likely to happen when a user tries to put the belt on his or her arm.

A belt of the folded-back type is shown in FIG. 12. What is shown in FIG. 12 is a cross-sectional view in longitudinal direction of a belt of the folded-back type having an inflatable pneumatic bag therein.

This belt comprises a band-shaped member "a" that is made of stretchable fabric into an end-closed tube-like shape, and an elongated air-tight inflatable pneumatic bag "b", as shown in FIGS. 12(A) to 12(C). The inflatable pneumatic bag "b" is housed within the band-shaped member "a" so that one end thereof is aligned with one end of the band-shaped member "a". The inflatable pneumatic bag "b" is shorter than the band-shaped member "a". Accordingly, the other end of the inflatable pneumatic bag "b" does not reach the other end of the band-shaped member "a". Provided on the outer side of the band-shaped member "a" at one end thereof is a ring "c" through which the band-shaped member "a" can be inserted.

This belt is wrapped around a proximal portion of an arm or leg of a person who receives the KAATSU muscle training, as shown in FIGS. 12(B) and 12(C). The symbol "L" in FIGS. 12(B) and 12(C) represents a cross section of an arm of a person who receives the KAATSU muscle training.

As shown in FIG. 12(B), when the belt is wrapped around the arm, one end of the band-shaped member "a" is in contact with a predetermined position on the arm, and the other end thereof comes full circle around the arm "L".

Then, as shown in FIG. 12(C), the other end of the band-shaped member "a" is inserted into the ring "c" and is folded back. Furthermore, the other end of the band-shaped member "a" is pulled in the direction depicted by the arrow in FIG. 12(C) to apply predetermined tension. Thus, the belt is tightened around the arm. An appropriate compression force is applied to the proximal portion of the arm by means of supplying and removing air into and from the inflatable pneumatic bag "b" of the belt via a tube which is not shown but is connected to the inflatable pneumatic bag "b".

This belt has a disadvantage in that when a user tries to pull the other end of the band-shaped member "a" in the state shown in FIG. 12(C), the whole band-shaped member "a" tends to rotate about the arm "L" (or leg) in the direction depicted by the arrow, as in the case of the belt of the straight type, so that it is difficult to place the belt with being tensioned appropriately. However, this belt forms a loop extending from its one end to the point of the ring "c" where it is folded back. When the other end of the belt is pulled, the arm "L" is tightened with the loop whose diameter is decreased. The belt is thus less likely to rotate during tightening the belt, as compared with the one of the straight type, and it is relatively easy to apply tension to the belt appropriately. However, rotation of the belt itself, if any, during tightening of the belt may result in undesirable positioning of the ring "c" to, for example, a position where it interferes with the body of a person receiving the KAATSU muscle training. This belt has greater negative effect of the rotation than the one of the straight type has. In addition, the inflatable pneumatic bag "b" in the belt of the type described is longer than the circumference of the target compressed site to allow for evenly compressing the target compressed site from all directions. Thus, the inflatable pneumatic bag "b" is also folded back at the position of the ring "c" where the belt is folded back. The inflatable pneumatic bag "b" is locally overloaded at and near the folding point. Besides, such bent of the inflatable pneumatic bag "b" may possibly divide the inner space of the inflatable pneumatic bag "b" into two compartments that communicates with each other, depending on the shape of the inflatable pneumatic bag "b" or the air pressure within the inflatable pneumatic bag "b". As a result, it becomes possible that the compression force which is achieved by the air pressure and which the belt applies to the arm "L" (or leg) cannot be controlled in an expected manner. This suggests that certain skill is required to place the belt in question with being tensioned appropriately, on the arm or leg, although the skill would be less than the one required for the belt of the straight type. In addition, this belt is not compatible with the belt having an inflatable pneumatic bag for the KAATSU muscle training.

The present invention is directed to provide a belt for the KAATSU muscle training which can easily be placed on an arm or leg and can be applied without trouble even when it comprises an inflatable pneumatic bag, and a KAATSU training apparatus in which such a belt is implemented.

SUMMARY OF THE INVENTION

In order to solve the aforementioned problems, the present inventor proposes a belt for KAATSU muscle training as described below (hereinafter, sometimes merely referred to as a "belt").

The present invention is based on a belt for KAATSU muscle training for the development of muscles that is used for applying a predetermined force for pressurization to a target compressed site near the proximal portion of one of the limbs of a user so that blood flow through the limb is restricted. Then, this belt comprises a band-shaped member having a band shape, and fastening means, an opening formed between one end of said band-shaped member and the other end thereof at a position closer to said other end such that a portion of said band-shaped member having a predetermined length from said one end can be inserted into the opening, the length of said band-shaped member from said one end to said opening being equal to or longer than the length that is enough to be wound around said target compressed site one complete turn, the length of said band-shaped member from said other end to said opening being shorter than the length that is enough to be wound around said target compressed site one complete turn, the belt being adapted to apply predetermined tension to said band-shaped member by means of pulling said one end of said band-shaped member and said other end thereof in opposite directions, with said target compressed site of the user being placed in a loop made of a part of said band-shaped member extending from said opening to an appropriate position on the side of said one end, the loop being generated by means of passing said one end of said band-shaped member through said opening, the belt being also adapted to keep the shape of said band-shaped member to which the predetermined tension is being applied, by means of said fastening means.

This belt has the opening into which the one end of the band-shaped member can be inserted, between the one end of the band-shaped member and the other end thereof. In addition, this belt is adapted to be placed on the target compressed site of the user while applying predetermined tension to said band-shaped member by means of pulling said one end of said band-shaped member and said other end thereof in opposite directions, with said target compressed site of the user being placed in a loop made of a part of said band-shaped member extending from said opening to an appropriate position on the side of said one end, the loop being generated by means of passing said one end of said band-shaped member through said opening. Final placement of the belt is made by maintaining the shape of said band-shaped member to which the predetermined tension is being applied, by means of said fastening means. With this belt, the band-shaped member can be tightened by means of pulling both ends of the band-shaped member in the opposite directions. Accordingly, with this belt, the user can pull the one end of the band-shaped member with his or her one hand while holding the other end with his or her other hand. Likewise, the user can pull the other end with his other hand while holding the one end with his or her one hand. Unlike the conventional belts, it is possible to avoid sliding rotation of the whole band-shaped member about the target compressed site when it is tightened.

What is required for the aforementioned opening is that it is formed in the band-shaped member between one end and the other end at a position closer to the other end, and a portion of said band-shaped member having a predetermined length from said one end (the portion may span over the whole range from one end of the band-shaped member to the opening) can be inserted into the opening.

The band-shaped member may be formed as an integrated part extending from one end to the other end. In such a case, the opening may be punched in a middle portion of the band-shaped member. Alternatively, a member having an opening may be attached to the band-shaped member at a middle portion thereof.

The band-shaped member may be comprised of a first band-shaped member extending from said one end of said band-shaped member to the opening and a second band-shaped member extending from said other end of said band-shaped member to said opening. In such a case, the belt for the KAATSU muscle training according to the present invention comprises a joint member that is connected to said first band-shaped member and said second band-shaped member, the joint member having an opening into which a portion of said first band-shaped member having a predetermined length from said one end can be inserted.

The joint member in the present invention may have a shape of, for example, a ring. The shape of the ring may appropriately be selected such as a rectangle or a circle.

The belt for KAATSU muscle training according to the present invention may comprise an air-tight inflatable pneumatic bag that is similar to the one provided in the conventional belts.

For example, in the belt for the KAATSU muscle training according to the present invention, an air-tight inflatable pneumatic bag may be provided along a predetermined range from said opening on the portion of said band-shaped member from said one end to said opening, the length of the inflatable pneumatic bag being equal to or longer than the length that is enough to be wound around said target compressed site one complete turn, the inflatable pneumatic bag being adapted to supply gas from the outside to the inside thereof and to remove the gas within it from the outside.

The length of the inflatable pneumatic bag in this case is equal to or longer than the length that is enough to be wound around the target compressed site one complete turn. This is for the purpose of allowing for evenly compressing the target compressed site from all directions. Although the length of the inflatable pneumatic bag is equal to or longer than the length that is enough to be wound around the target compressed site one complete turn, the circumference of the target compressed site varies among different individuals. Besides, even for the same person, it varies over time longer than a certain period due to some factors including past training. Accordingly, it is preferable that the length of the inflatable pneumatic bag be longer than the circumference of the target compressed site of a person who is expected to use that belt by, for example, approximately 10% to 50%. The length of the inflatable pneumatic bag does not necessarily correspond to the entire length from the opening to the one end of the band-shaped member. The inflatable pneumatic bag may be provided over a range from the opening in the band-shaped member to a position between the opening and the one end.

When the belt having the inflatable pneumatic bag is placed on the target compressed site of the user, as in the case of the aforementioned belt, the target compressed site of the user is placed in a loop made of a part of the band-shaped member extending from the opening to an appropriate position on the side of the one end, the loop being generated by means of passing the one end of the band-shaped member through the opening. Under such a state, the one end and the other end of the band-shaped member are pulled in the opposite directions. Even when the inflatable pneumatic bag is longer than the circumference of the target compressed site, the inflatable pneumatic bag will not be folded back more than the length of the circumference of the target compressed site. Accordingly, this belt is free from the problems of any overload of the inflatable pneumatic bag or two compartments generated within the inflatable pneumatic bag when the inflatable pneumatic bag in the conventional belt is folded back.

The inflatable pneumatic bag may be applied to the belt as described above which comprises the first band-shaped member, the second band-shaped member, and the joint member.

The inflatable pneumatic bag in this case is air-tight as in the aforementioned case, and is adapted to supply gas from the outside to the inside thereof and to remove the gas within it from the outside. In addition, the length of the inflatable pneumatic bag is equal to or longer than the length that is enough to be wound around said target compressed site one complete turn. The inflatable pneumatic bag extends along a predetermined range from the proximal portion of said first band-shaped member where said first band-shaped member is connected to said joint member.

The inflatable pneumatic bag may be provided on an appropriate portion of the band-shaped member such as on the inner surface. When the band-shaped member has a hollow tube-like shape, the inflatable pneumatic bag may be housed in the band-shaped member. When said first band-shaped member has a hollow tube-like shape, said inflatable pneumatic bag may be housed in said first band-shaped member.

In the present invention, the fastening means may be any means as long as it can keep the shape of the band-shaped member to which predetermined tension is being applied.

For example, said fastening means may be comprised of a first hook-and-loop fastener that is provided on the outer surface of said band-shaped member at a position where said loop is to be formed; a second hook-and-loop fastener that is provided on the inner surface of said band-shaped member over a predetermined range from said one end of said band-shaped member, the second hook-and-loop fastener being adapted to be removably attached to said first hook-and-loop fastener; and a third hook-and-loop fastener that is provided on the inner surface of said band-shaped member over a predetermined range from said other end of said band-shaped member, the third hook-and-loop fastener being adapted to be removably attached to said first hook-and-loop fastener. (It is noted that the terms “inner” and “outer” in terms of the band-shaped member as used herein refer to the “closer” and “farther” sides, respectively, of the belt for the KAATSU muscle training, with respect to the target compressed site of the user when the belt is wrapped around the target compressed site of the user.)

In this case, the shape of the belt can be kept by means of engaging the first hook-and-loop fastener and the second hook-and-loop fastener with each other, and engaging the first hook-and-loop fastener and the third hook-and-loop fastener with each other. When the fastening means is comprised of such first, second, and third hook-and-loop fasteners, it is preferable that the total length of the band-shaped member according to the present invention be slightly shorter than twice the circumference of the expected target compressed site. This ensures that the one end of the band-shaped member is not overlapped with the other end thereof when the first hook-and-loop fastener and the second hook-and-loop fastener are engaged with each other, and the first hook-and-loop fastener and the third hook-and-loop fastener are engaged with each other. This allows the aforementioned placement to be done securely.

Said fastening means may comprise a fourth hook-and-loop fastener that is provided on the outer surface of said band-shaped member over a predetermined range from said other end of said band-shaped member to said opening, the fourth hook-and-loop fastener being adapted to be removably attached to said second hook-and-loop fastener. With this, if the one end of the band-shaped member is overlapped with the other end thereof when the first hook-and-loop fastener and the second hook-and-loop fastener are engaged with each other and when the first hook-and-loop fastener and the third hook-and-loop fastener are engaged with each other because the circumference of the target compressed site of the user is slightly shorter than expected, the second hook-and-loop fastener on the inner surface of the band-shaped member at the one end thereof can be engaged with the fourth hook-and-loop fastener on the outer surface of the band-shaped member at the other end thereof.

What is required for the band-shaped member is that it has a band shape. As described above, it may have a tube-like shape. Any material may be used for the production of the band-shaped member, and the material may be stretchable in the longitudinal direction thereof. When the user performs exercises with the belt being placed on the target compressed site, it is possible that the belt compresses contracting bigger muscles excessively and the force for pressurization exerted by the belt on the muscles becomes too much. If this happens, no one can dismiss the possibility of excessive blood restriction and safety concerns. On the contrary, this sort of problems can be avoided by using the band-shaped member that is at least stretchable in the longitudinal direction.

When the belt according to the present invention comprises the inflatable pneumatic bag, the inflatable pneumatic bag may be stretchable in the longitudinal direction thereof. As apparent from the above, even when the band-shaped member is stretchable in the longitudinal direction thereof, the inflatable pneumatic bag has the potential for preventing stretch of the band-shaped member if the inflatable pneumatic bag is not stretchable in the longitudinal direction thereof. In order to avoid this, the inflatable pneumatic bag may be rendered stretchable in the longitudinal direction.

By utilizing the belt having the inflatable pneumatic bag out of the aforementioned belts for the KAATSU muscle training, it is possible to implement a KAATSU muscle training apparatus as described below.

The KAATSU muscle training apparatus comprises at least one belt for KAATSU muscle training for the development of muscles that is used for applying a predetermined force for pressurization to a target compressed site near the proximal portion of at least one of the limbs of a user so that blood flow through the limb is restricted; and a main device having a pump, the main device being used in combination with said belt. In addition, said belt of this KAATSU muscle training apparatus comprises a band-shaped member having a band shape, an opening formed between one end of said band-shaped member and the other end thereof at a position closer to said other end such that a portion of said band-shaped member having a predetermined length from said one end can be inserted into the opening, the length of said band-shaped member from said one end to said opening being equal to or longer than the length that is enough to be wound around said target compressed site one complete turn, the length of said band-shaped member from said other end to said opening being shorter than the length that is enough to be wound around said target compressed site one complete turn, an air-tight inflatable pneumatic bag being provided along a predetermined range from said opening on the portion of said band-shaped member from said one end to said opening of the belt, the length of the inflatable pneumatic bag being equal to or longer than the length that is enough to be wound around said target compressed site one complete turn, the inflatable pneumatic bag being adapted to supply gas from the outside to the inside thereof and to remove the gas within it from the outside. Furthermore, said main device is adapted to supply air into said inflatable pneumatic bag or to remove air from said inflatable pneumatic bag by using the pump thereof.

BEST MODES FOR CARRYING OUT THE INVENTION

Figure 1:
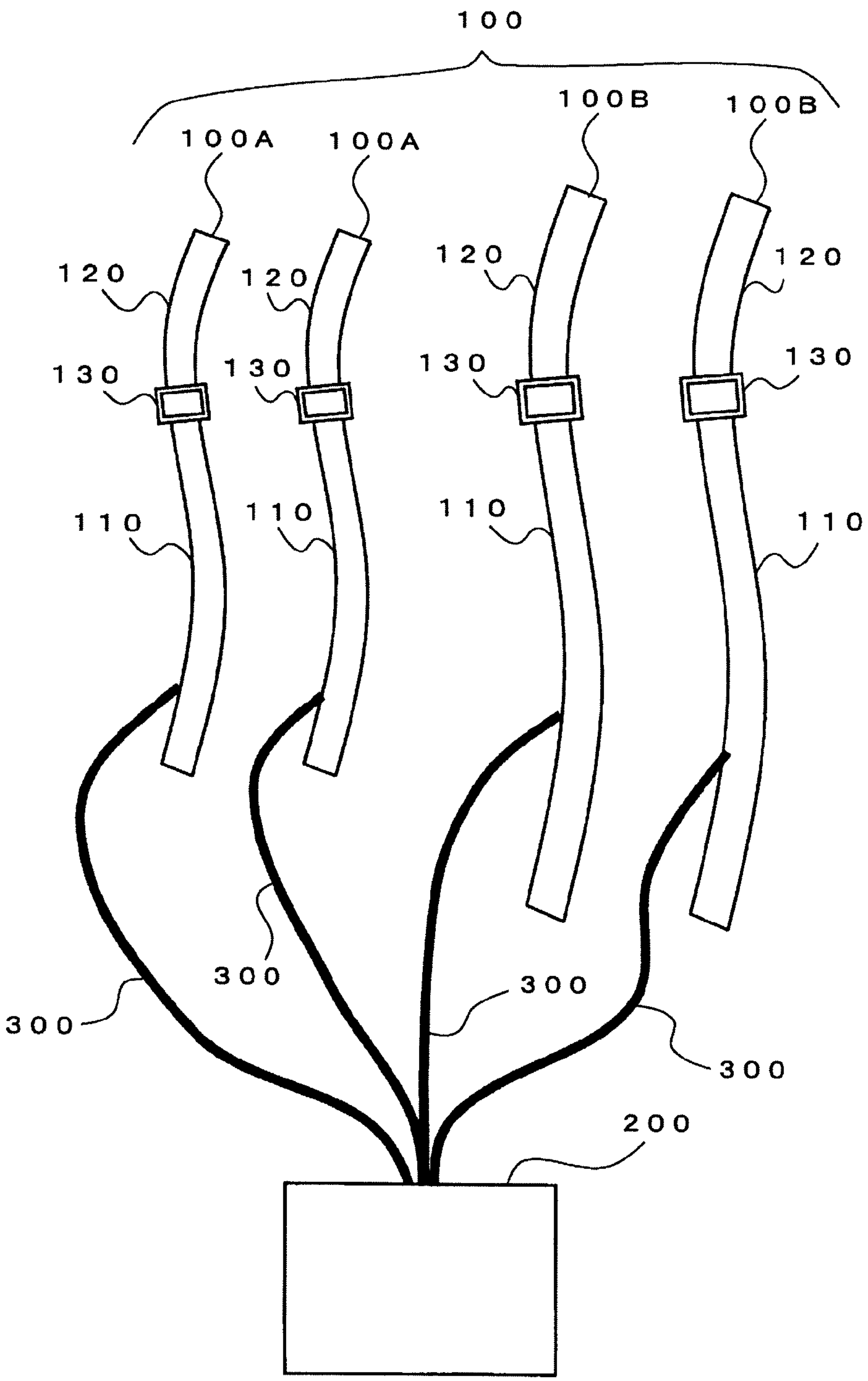
FIG. 1 is a view schematically showing the entire configuration of a KAATSU muscle training apparatus of a first embodiment of the present invention.

Preferred first and second embodiments of the present invention are described now with reference to the drawing. In the description of both embodiments, similar components and parts are depicted by the like reference numerals, and any redundant description will be omitted.

First Embodiment

FIG. 1 is a view schematically showing the entire configuration of a KAATSU muscle training apparatus according to a first embodiment of the present invention.

As shown in FIG. 1, the KAATSU muscle training apparatus according to this embodiment comprises a belt 100 and a main device 200. Each component of the belt 100 is designed so that it can be connected to the main device 200 through, for example, a connecting pipe 300 comprised of a rubber tube.

The belt 100 in this embodiment comprises a plurality of, more specifically, four components as shown in FIG. 1. The reason why there are four components of the belt 100 is to allow secure placement of the components of the belt 100 on the arms and legs, respectively, of a person (user) who uses the KAATSU muscle training method. The components of the belt 100 are tightened around a predetermined range (target compressed site) near the proximal portion of the arms and legs of the user.

Of the four components of the belt 100, belts 100A are for arms (each of which is intended to be wrapped around an arm for the compression of the target compressed site on the arm) while belts 100B are for legs (each of which is intended to be wrapped around a leg for the compression of the target compressed site on the leg). The number of the components of the belt 100 is not necessarily four. Any number equal to or larger than one may be used. The number of the belt(s) 100A for arms is not necessarily identical with the number of the belt (s) 100B for legs. More than four components of the belt 100 may be provided to cope with cases where two or more persons perform the KAATSU muscle training at the same time.

Figure 2:
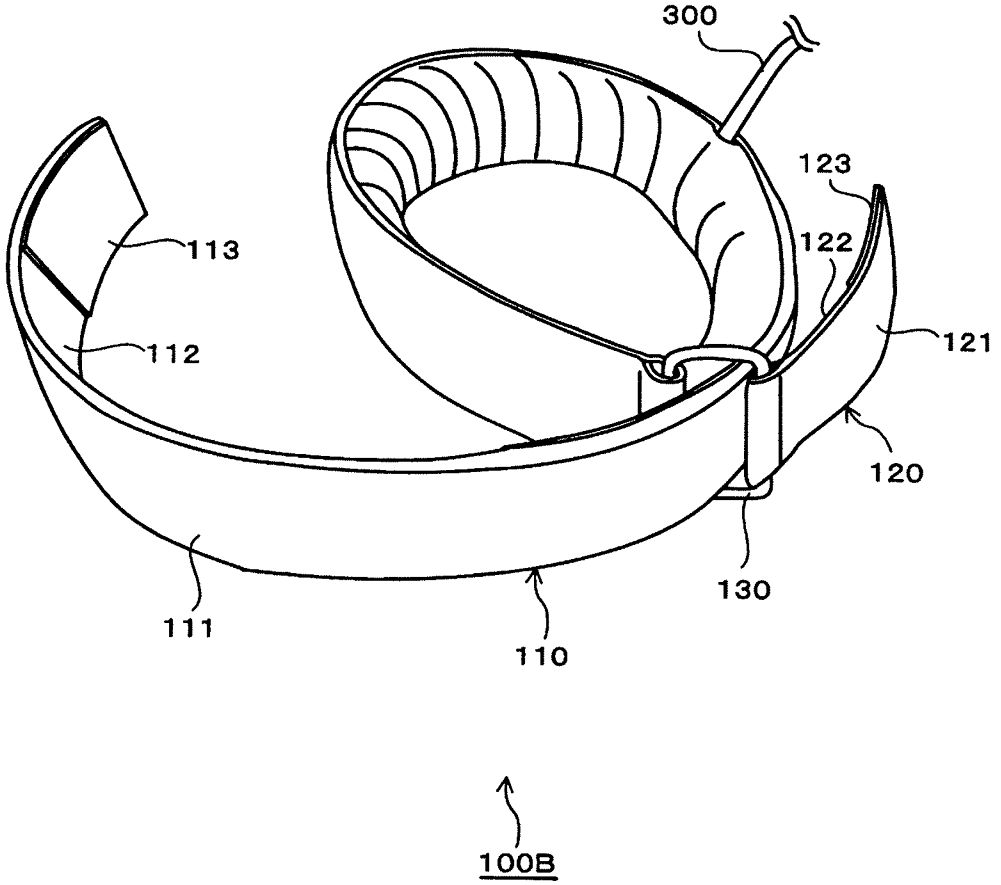
FIG. 2 is a perspective view showing a belt included in the KAATSU muscle training apparatus in FIG. 1.
Figure 3:
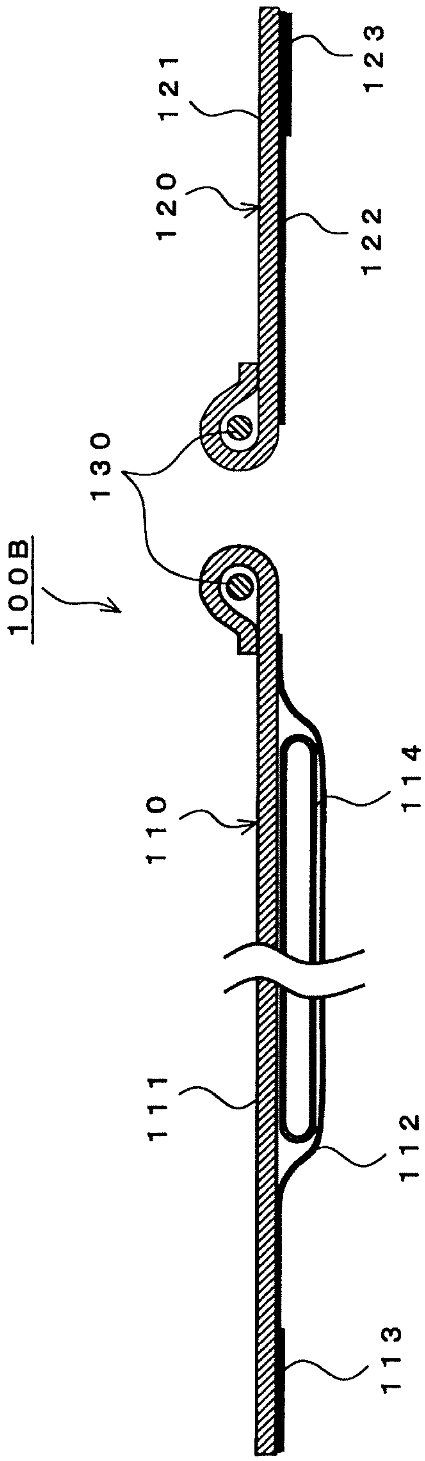
FIG. 3 is a cross-sectional view showing the belt included in the KAATSU muscle training apparatus in FIG. 1.

The belt 100 in this embodiment is structured as shown in FIGS. 1, 2, and 3. FIG. 2 is a perspective view showing an embodiment of the belt 110B for legs. FIG. 3 is a cross-sectional view in longitudinal direction of the belt 100B.

The belt 100 in this embodiment is intended to be wrapped around a target compressed site of a limb. It is intended to apply a predetermined compression force to the target compressed site, and is adapted so that the compression force to be applied to a predetermined range of the arm or the leg can be varied in a manner described below.

Regardless of whether it is for use in arms or legs, each component of the belt 100 comprises a first band-shaped member 110 and a second band-shaped member 120 both of which have an elongated shape, and a joint member 130.

The joint member 130 is connected to the proximal end (the end closer to the joint member 130) of the first band-shaped member 110 and the proximal end (the end closer to the joint member 130) of the second band-shaped member 120. The joint member 130 has an opening through which the first band-shaped member 110 can be passed. It has a rectangular ring shape in this embodiment, but is not necessarily so. The first band-shaped member 110 and the second band-shaped member 120 are attached to the opposing sides, respectively, of the joint member 130.

The total length of the belt 100, i.e., the combined length of the first band-shaped member 110, the second band-shaped member 120, and the joint member 130, may be determined in accordance with the girth of the target compressed site of a person who uses the KAATSU muscle training method. The total length of the belt 100 should be at least longer than the length of the girth of the target compressed site of the user. The total length of the belt 100 in this embodiment is approximately twice as long as the girth of the target compressed site of the user (the length is twice ±20% as long as the expected length of the girth of the target compressed site). In order to meet requirements for all expected users, the belts 100A and the belts 100B of different total lengths are provided.

The total length of the belt 100A for arms according to this embodiment is determined in view of the girth of the target compressed site on the arm of the user being 26 cm. More specifically it is approximately 50 cm. The total length of the belt 100B for legs is determined in view of the girth of the target compressed site on the leg of the user being 45 cm. More specifically, it is approximately 80 cm.

The first band-shaped member 110 is longer than the second band-shaped member 120. The first band-shaped member 110 should have a length that is enough to be wound around the target compressed site of the user one complete turn or more. The length of the first band-shaped member 110 of the belt 100A for arms according to this embodiment is approximately 40 cm in view of the girth of the target compressed site on the arm of the user being 26 cm, which is not necessarily so. On the other hand, the length of the second band-shaped member 120 of the belt 100A for arms is approximately 10 cm. The length of the first band-shaped member 110 of the belt 100B for legs according to this embodiment is approximately 65 cm in view of the girth of the target compressed site on the leg of the user being 45 cm, which is not necessarily so. On the other hand, the length of the second band-shaped member 120 of the belt 100B for legs is approximately 15 cm. It is noted that the only requirement for the length of the second band-shaped member 120 is that it is not inconvenient for a person to grasp it, irrespective of the belt 100A for arms and the belt 100B for legs. The lengths of the first and second band-shaped members 110 and 120 are determined in consideration with this requirement, plus the requirement for the first band-shaped member 110 that it should be longer than the girth of the target compressed site plus the requirement that the total length of the belt 100 is approximately twice as long as the length of the girth of the target compressed site of the user.

In this embodiment, the first band-shaped member 110 has a constant width along the entire length thereof for both of the belt 100A for arms and the belt 100B for legs, which is not necessarily so. The same applies to the second band-shaped member 120. In addition, in this embodiment, the width of the first band-shaped member 110 is identical to the width of the second band-shaped member 120 for both of the belt 100A for arms and the belt 100B for legs, which is not necessarily so. The widths of the first band-shaped member 110 and the second band-shaped member 120 may appropriately be determined in view of whether the target compressed site is on an armor on a leg. For example, for the belt 100A for arms, the widths of the first band-shaped member 110 and the second band-shaped member 120 may be approximately 3 cm to 3.5 cm. For the belt 100B for legs, the widths of the first band-shaped member 110 and the second band-shaped member 120 may be approximately 5 cm to 5.5 cm.

The first band-shaped member 110 has the outer surface that is made of a thick fabric 111 and the inner surface that is made of a thin fabric 112.

The thick fabric 111 of the first band-shaped member 110 is connected to the joint member 130 at the proximal end thereof. The connection between the first band-shaped member 110 and the joint member 130 may be achieved in any way. For example, as shown in FIG. 3, the proximal end of the thick fabric 111 may be passed through the opening in the joint member 130, folded back on itself and stitched to the overlapping surface of the thick fabric 111. The connection between the second band-shaped member 120 and the joint member 130 is also achieved as in the case of the connection between the first band-shaped member 110 and the joint member 130.

The thick fabric 111 in this embodiment is a piece of fabric having a width of approximately 3 mm and is resilient to a certain extent. The thick fabric 111 is stretchable in its longitudinal direction. The thin fabric 112 in this embodiment is a piece of fabric having a width of 0.5 mm. The thin fabric 112 is made of a soft material that is comfortable to the touch by the user because it will be in contact with the target compressed site of the user when the belt 100 is securely placed on the target compressed site of the user. The thin fabric 112 is also stretchable in its longitudinal direction. Since the thick fabric 111 and the thin fabric 112 are both stretchable, the first band-shaped member 110 is stretchable in its longitudinal direction.

The outer surface of the thick fabric 111 is a surface that can be removably engaged with a second hook-and-loop fastener and a third hook-and-loop fastener described below. It virtually serves as a first hook-and-loop fastener in the present invention. The inner surface of the thick fabric 111 at the distal end thereof (the end that is away from the joint member 130) is provided with a second hook-and-loop fastener 113 having a length of 4 to 5 cm, which is not necessarily so. The second hook-and-loop fastener 113 is made of a Velcro tape.

The thick fabric 111 and the thin fabric 112 are connected to each other along the longitudinal sides thereof by means of, for example, stitching. The thick fabric 111 and the thin fabric 112 are connected to each other only along their sides in a predetermined distance from the joint member 130. Accordingly, the portion of the first band-shaped member 110 extending from the joint member 130 to that point is a tube-like object. An inflatable pneumatic bag 114 is provided within the tube-like first band-shaped member 110.

The inflatable pneumatic bag 114 is an elongated air-tight bag that is stretchable at least in its longitudinal direction. The inflatable pneumatic bag 114 is made of, but not limited to, a raw rubber in this embodiment. As shown in FIG. 2, the inflatable pneumatic bag 114 is connected to one end of the connecting pipe 300. The aforementioned connection between the thick fabric 111 and the thin fabric 112 along their longitudinal sides is not made at the position through which the connecting pipe 300 is passed so that the connecting pipe 300 can be introduced into the first band-shaped member 110. The inflatable pneumatic bag 114 is supplied with air from the main device 200 through the connecting pipe 300. The air within the inflatable pneumatic bag 114 is removed by the main device 200. Such delivery and release of air into and from the inflatable pneumatic bag 114 is performed by the main device 200.

The length of the inflatable pneumatic bag 114 is such that it can wrap around the target compressed site at least one turn. The length of the inflatable pneumatic bag 114 in the belt 100A for arms according to this embodiment is approximately 35 cm in view of the girth of the target compressed site on the arm of the user being 26 cm. The length of the inflatable pneumatic bag 114 in the belt 100B for legs according to this embodiment is approximately 55 cm in view of the girth of the target compressed site on the arm of the user being 45 cm. The length of the inflatable pneumatic bag 114 may be determined so that it is approximately 10% to 50% longer than the girth of the target compressed site.

The second band-shaped member 120 is, briefly speaking, identical in structure to the first band-shaped member 110 except that there is no inflatable pneumatic bag 114.

The second band-shaped member 120 has the outer surface that is made of a thick fabric 121 and the inner surface that is made of a thin fabric 122. The thick fabric 121 and the thin fabric 122 of the second band-shaped member 120 are made of a material similar to the one used for the thick fabric 111 and the thin fabric 112, respectively, of the first band-shaped member.

The thick fabric 121 and the thin fabric 122 are connected to each other by means of stitching in this embodiment.

The outer surface of the thick fabric 121 is a surface that can be removably engaged with the second hook-and-loop fastener 113. It virtually serves as a fourth hook-and-loop fastener in the present invention. The inner surface of the thick fabric 121 at the distal end thereof (the end that is away from the joint member 130) is provided with a third hook-and-loop fastener 123 having a length of 4 to 5 cm, which is not necessarily so. The third hook-and-loop fastener 123 is made of a Velcro tape.

Next, a configuration of the main device 200 is described.

The main device 200 is capable of supplying gas into the inflatable pneumatic bag 114 and removing the gas from the inflatable pneumatic bag 114. The control that is carried out by the main device 200 for supplying and removing the gas into and from the inflatable pneumatic bag 114 is achieved automatically in this embodiment, which is not necessarily so. The main device 200 may have any configuration as long as it can supply the gas into the inflatable pneumatic bag 114 and removes the gas from the inflatable pneumatic bag 114, and as long as it can achieve the aforementioned automatic control. The main device 200 may be those disclosed in, for example, Japanese Patent Laid-Open Nos. 2007-125254, 2005-58544, and 2005-6921.

Figure 4:
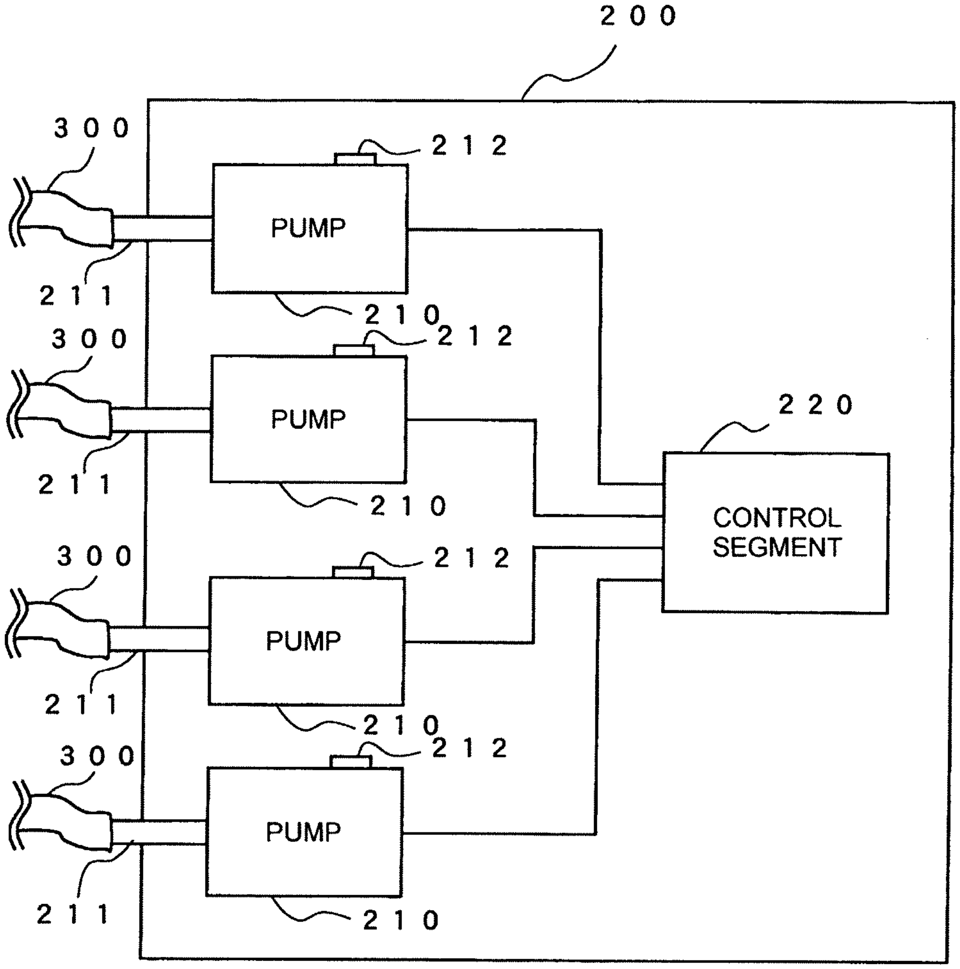
FIG. 4 is a view schematically showing an internal configuration of the main device included in the KAATSU muscle training apparatus in FIG. 1.

A configuration of an exemplary main device 200 is schematically shown in FIG. 4. As shown in FIG. 4, the main device 200 is composed of four pumps 210 and a control segment 220. In this embodiment, the main device 200 comprises a casing in which the pumps 210 and the control segment 220 are housed. An input device is provided outside the casing but is not illustrated herein.

Each of the four pumps 210 is associated with one of the four components of the belt 100.

The pump 210 has a function of sucking the surrounding air and supplying it to the outside through a pump connection port 211 which will be described below. The pump 210 includes a valve 212. By opening the valve 212, the gas in the pump 210 can be discharged to the outside. Each of the four pumps 210 has its own pump connection port 211 and is connected to the inflatable pneumatic bag 114 through the connecting pipe 300 connected thereto. When the pump 210 forces the gas, the gas is introduced into the inflatable pneumatic bag 114. When the pump 210 opens the valve 212, the gas can be removed from the inflatable pneumatic bag 114. The valve 212 is not necessarily provided in the pump 210. It may be disposed at any point along the path from the pump 210 to the inflatable pneumatic bag 114.

The pump 210 contains a pressure gauge which is not shown in order to measure the air pressure within the pump 210. The air pressure within the pump 210 is obviously equal to the air pressure within the inflatable pneumatic bag 114.

The control segment 220 is for controlling the pumps 210. The control segment 220 performs control to activate the pump 210 in order to introduce the air into the inflatable pneumatic bag 114 in the belt 100 while the valve 212 is closed, and to open the valve 212 in the pump 210 to remove the air from the inflatable pneumatic bag 114. In other words, the control segment 220 controls the pump 210 in addition to the opening and closing of the valve 212.

Figure 5:
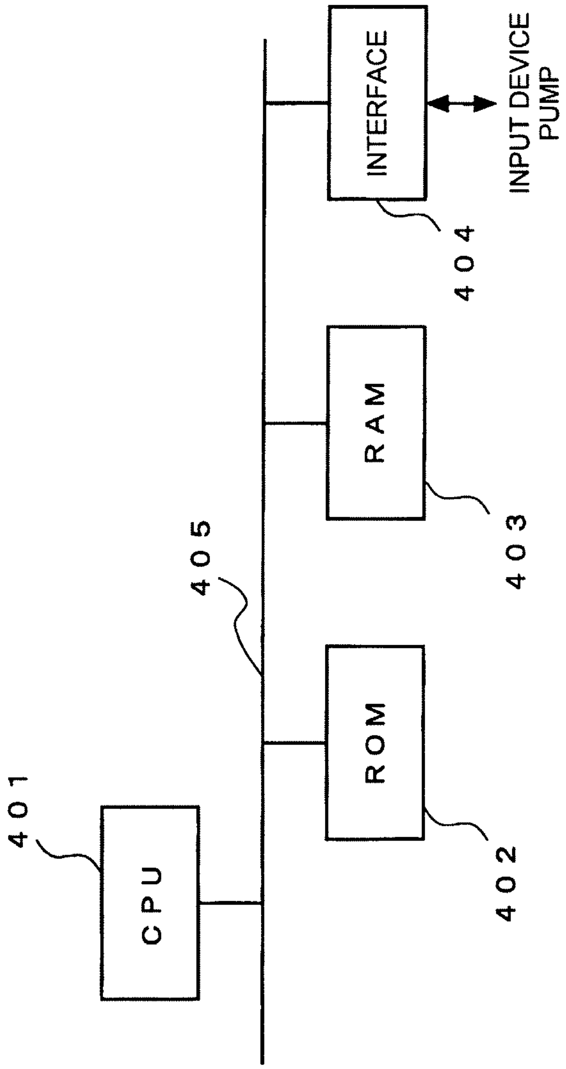
FIG. 5 is a hardware configuration of the control segment included in the KAATSU muscle training apparatus in FIG. 1.

An internal configuration of the control segment 220 is schematically shown in FIG. 5. The control segment 220 contains a computer wherein a CPU 401, an ROM 402, an RAM 403 and an interface 404 are connected to each other through a bus 405.

The CPU 401 is a central processing unit that controls the whole control segment 220. The ROM 402 records a program and data that are necessary for the processing described below in which the processing is carried out by the control segment 220. The CPU 401 executes the processing based on the program. The ROM 402 may be embodied by using a flash ROM. Instead of the ROM 402, or in addition to the ROM 402, the control segment 220 may comprise other recording medium such as a hard disk on which the aforementioned program and the data are recorded. The RAM 403 is for providing a working area for the execution of the aforementioned program. The interface 404 has functions of receiving an input from the input device and sending an instruction from the control segment 220 to each of the four pumps 210.

Figure 6:
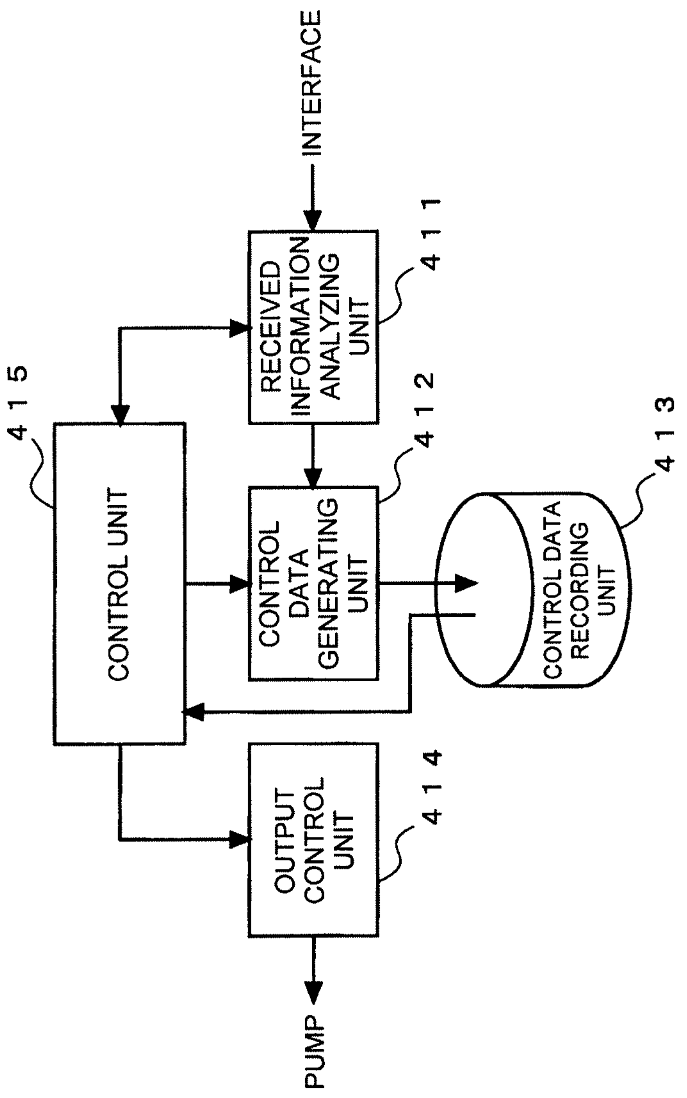
FIG. 6 is a view showing a functional block generated in the control segment included in the KAATSU muscle training apparatus in FIG. 1.

As the CPU 401 executes the aforementioned program, a functional block as shown in FIG. 6 is created within the control segment 220.

The control segment 220 includes a received information analyzing unit 411, a control data generating unit 412, a control data recording unit 413, an output control unit 414, and a control unit 415.

The received information analyzing unit 411 receives an input supplied from the input device, via the interface 404 and analyzes the details thereof. Data representing the result of the analysis by the received information analyzing unit 411 are supplied to the control data generating unit 412 or the control unit 415.

The control data generating unit 412 is for generating control data for use in controlling the pump 210 including the opening and closing of the valve 212, according to the data received from the received information analyzing unit 411. The control data generating unit 412 is adapted to record the generated control data on the control data recording unit 413.

The control data recording unit 413 is for recording the control data received from the control data generating unit 412. On the control data recording unit 413 in this embodiment, the control data associated with the respective one of the four pumps 210 are recorded as a set. In addition, the control data recording unit 413 in this embodiment is adapted to record two or more sets of the control data for the four pumps 210. A single set of the data is for controlling compression of the arms and the legs during the KAATSU muscle training. The two or more sets of the data may be those for two or more persons. In such a case, the data is read for a user who receives the KAATSU muscle training depending on who receives the KAATSU muscle training. In addition, the two or more sets of the data may be those for one specific person who receives the KAATSU muscle training. In such a case, the person may use different data that are read depending on, for example, physical conditions. The number of the sets of the data may be equal to the number of the persons and each set may include different data.

The control unit 415 is for totally controlling the received information analyzing unit 411, the control data generating unit 412, and the output control unit 414. In addition, it has a function of controlling the modes described below. The control unit 415 has functions of reading a set of control data from the control data recording unit 413 and sending them to the output control unit 414 when the KAATSU muscle training is performed.

The output control unit 414 has a function of controlling the pump 210 according to the control data. The KAATSU muscle training is performed while the output control unit 414 is controlling the pump 210.

Next, how the KAATSU muscle training is performed by using this main device 200 is described.

First, the control data is generated.

The main device 200 of the present invention is adapted to carry out two modes: a control mode and a training mode. The control data is generated in the control mode.

An input about which one of the control mode and the training mode is to be selected is made by using the input device. When information indicating which one of the control mode and the training mode is to be selected is supplied from the input device, the received information analyzing unit 411 which receives the information through the interface 404 transfers it to the control unit 415. In response to this, the control unit 415 begins to use the control mode or the training mode.

In this main device 200, it is possible to enter the information that is necessary for the generation of the control data, by means of manipulating the input device during the time when the control mode is active. The entered information is transmitted to the control data generating unit 412 through the interface 404 and the received information analyzing unit 411. The control data generating unit 412 generates the control data according to the received information, and transmits it to the control data recording unit 413. The control data recording unit 413 records that data. As described above, as to the control data in this embodiment, four data corresponding to the respective four pumps 210 are combined as a single set. The control data is the one that indicates in what way the air pressure in the pump 210 should be changed over time.

In this embodiment, two or more sets each having four control data are recorded on the control data recording unit 413, so that the aforementioned processing is repeated as many times as necessary. Thus, in this embodiment, the control data suitable for different individuals who receive the KAATSU muscle training are generated in a so-called custom-made manner.

It is noted that typical or general-purpose control data may be recorded on the control data recording unit 413 before shipping the main device 200. The number of the control data to be recorded on the control data recording unit 413 may be equal to or larger than one.

After the control data is generated, the main device 200 is connected to the belt 100 through the connecting pipe 300. Next, the belt 100 is wrapped around the target compressed site on the arm or the leg of the user.

How the belt 100 is securely placed on the target compressed site is as follows.

[When User Places Belt on His or Her Own Leg]

Figure 7:
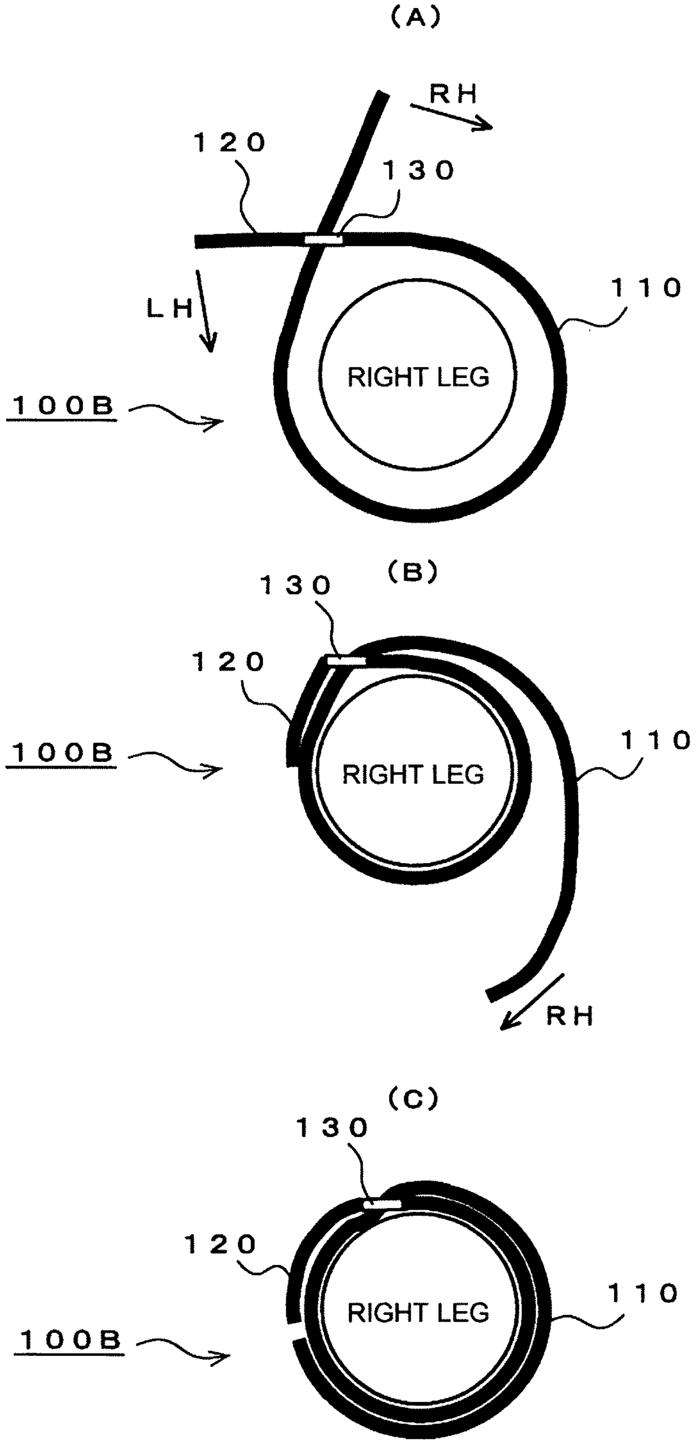
FIG. 7 is a plane cross-sectional view illustrating how the belt included in the KAATSU muscle training apparatus in FIG. 1 is placed on the right leg of a user.

The belt 100B for legs is placed on the user's own leg in a manner as shown in FIG. 7. FIGS. 7(A) to 7(C) illustrate a procedure to place the belt 100B on the target compressed site on the right leg. A cross-section of the right thigh is seen from the above, and the upper side with respect to the paper surface corresponds to the user's front thigh.

In order to place the belt 100B for legs on the user's own leg, the distal end of the first band-shaped member 110 of the belt 100B is inserted into the opening in the joint member 130 to form a loop of the first band-shaped member 110, and then the right leg is passed through the loop as shown in FIG. 7(A). For this purpose, it is easier to take steps of forming a loop as described above, inserting the right foot into it, and then moving up the belt 100B towards the proximal portion of the leg.

In this state, the distal end of the first band-shaped member 110 is held with the right hand and is pulled in the direction depicted by the arrow RH. The distal end of the second band-shaped member 120 is held with the left hand and is pulled in the direction depicted by the arrow LH. This reduces the size of the aforementioned loop of the first band-shaped member 110, applying an appropriate tension to the belt 100B.

Then, the user further pulls the second band-shaped member 120 with his or her left hand. The third hook-and-loop fastener 123 on the inner surface of the second band-shaped member 120 at the end thereof is engaged with the thick fabric 111 of the outer surface of the first band-shaped member 110, as shown in FIG. 7(B).

Next, the user further pulls the first band-shaped member 110 with his or her right hand in the direction depicted by the arrow RW in FIG. 7(B). Then, the second hook-and-loop fastener 113 on the inner surface of the first band-shaped member 110 at the end thereof is engaged with the thick fabric 111 of the outer surface of the first band-shaped member 110, as shown in FIG. 7(C). If the user has a slim leg or the belt 100B is stretched more than as usual because higher tension is applied to the belt 100B, the distal end of the first band-shaped member 110 may be overlapped with the distal end of the second band-shaped member 120. In such a case, the second hook-and-loop fastener 113 on the inner surface of the first band-shaped member 110 at the end thereof may be engaged with the thick fabric 121 of the outer surface of the second band-shaped member 120.

In this way, the user can securely place the belt 100B on his or her right leg.

Tightening the belt 100B on his or her left leg can be achieved by using the same procedures as shown in FIG. 7 although all relationships reverse, as in a mirror image with respect to FIG. 7.

[When Someone Places Belt on User's Arm or Leg]

For this purpose, the same procedures are used as those described in conjunction with the case where the user places the belt 100B on his or her own leg to let a third person place the belt 100A or the belt 100B on the user's arm or leg, respectively.

[When User Places Belt on His or Her Own Arm]

Figure 8:
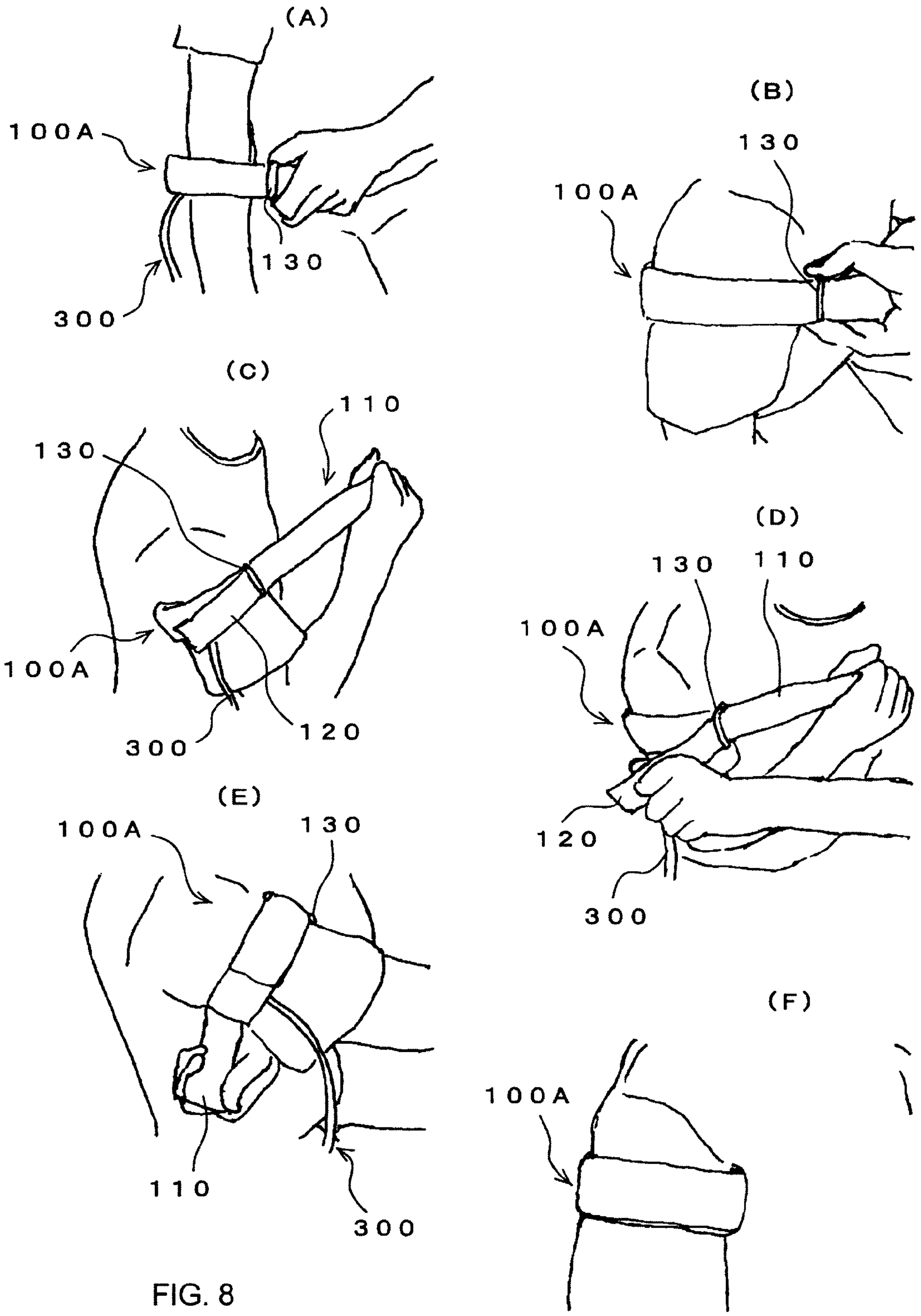
FIG. 8 is a plane cross-sectional view illustrating how the belt included in the KAATSU muscle training apparatus in FIG. 1 is placed on the right arm of a user.

For this purpose, the belt is going to be placed through slightly different procedures from those described above. This is described with reference to FIG. 8.

In order to place the belt 100A on his or her own arm, the distal end of the first band-shaped member 110 of the belt 100A is inserted into the opening in the joint member 130 to form a loop of the first band-shaped member 110 as shown in FIG. 2.

Then, either arm is passed through the loop (FIG. 8(A)) and moves up the belt 100A with the hand of the other arm towards the proximal portion of the arm (FIG. 8(B)). In this case, care should be taken so that the first band-shaped member 110 is positioned on the armpit side and the second band-shaped member 120 is positioned on the opposite side.

In this state, the user holds the distal end of the first band-shaped member 110 with the hand of the arm passing through the loop of the first band-shaped member 110 (FIG. 8(C)). The arm on the same side as the hand holding the distal end of the first band-shaped member 110 is bent at the elbow towards the shoulder.

The user then holds the second band-shaped member 120 with the hand on the side opposite to the arm passing through the loop of the first band-shaped member 110, and pulls the second band-shaped member 120 outer downwards with respect to the arm passing through the loop (FIG. 8(D)). As described above, the first band-shaped member 110 is held with the hand on the same side as the arm passing through the loop, so that the belt 110A does not rotate around the target compressed site on the arm. In this state, by using the process similar to the one illustrated in FIG. 7(B), the third hook-and-loop fastener 123 on the inner surface of the second band-shaped member 120 at the end thereof is engaged with the thick fabric 111 of the outer surface of the first band-shaped member 110.

Next, the hand holding the distal end of the first band-shaped member 110 on the same side as the arm passing through the loop is released therefrom, and the distal end of the first band-shaped member 110 is held with the opposite hand. The distal end of the first band-shaped member 110 is pulled under the arm passing through the loop, in the direction away from the body to apply a desired tension to the first band-shaped member 110 (FIG. 8(E)). Then, the second hook-and-loop fastener 113 on the inner surface of the first band-shaped member 110 at the end thereof is engaged with the thick fabric 111 of the outer surface of the first band-shaped member 110, as shown in FIG. 7(C). In this case, if necessary, the second hook-and-loop fastener 113 on the first band-shaped member 110 may be engaged with the thick fabric 121 on the outer surface of the second band-shaped member 120, as in the case described above.

In this way, the user can place the belt 100A on his or her own arm (FIG. 8(F)).

Then, the main device 200 is switched to the training mode to perform the KAATSU muscle training. In order to direct the main device 200 to carry out the training mode, the input device can appropriately be manipulated as described above.

When the training mode begins, the user who receives the KAATSU muscle training manipulates the input device to select a set of four control data intended to be used for him or her. If there are two or more sets of the control data, then an appropriate set of the control data is selected in view of, for example, his or her physical conditions. The user can select the control data by using the input device. When the information indicating which set of the control data is selected is supplied from the input device, this information is transmitted to the control unit 415 through the interface 404 and the received information analyzing unit 411. The control unit 415 reads the control data indicated by this information out of the control data recording unit 413 and transmits them to the output control unit 414. The output control unit 414 controls the pumps 210 according to the control data. The pump 210 automatically keeps the air pressure within the pump 210 to a level indicated by the control data while measuring the air pressure within the pump 210 by using the pressure gauge, and in turn, keeps the air pressure within the inflatable pneumatic bag 114 to an appropriate level.

The magnitude of the air pressure within the inflatable pneumatic bag 114 and how long a given air pressure is continued depend on the age, gender, exercise history, physical condition, and the like, which are controlled appropriately by the aforementioned control data. The blood flow into the limb distal to the target compressed site of the compressed arm or leg of the user is restricted, which artificially produce exercising arms or legs. The arms and legs, in this embodiment, are not compressed simultaneously.

The KAATSU muscle training is performed in the manner described above. During the time when the target compressed site is applied with the compression force by the belt 100, the user may be placed at rest or may perform exercises though light.

When the user performs exercises, it may be better that the connecting pipe 300 can be separated into two parts. In such a case, the part of the connecting pipe on the belt 100 may have a mechanism such as a valve to prevent the air within the inflatable pneumatic bag 114 from being escaped.

After the KAATSU muscle training, the user removes the belt.

<<Modified Version>>

Figure 9:
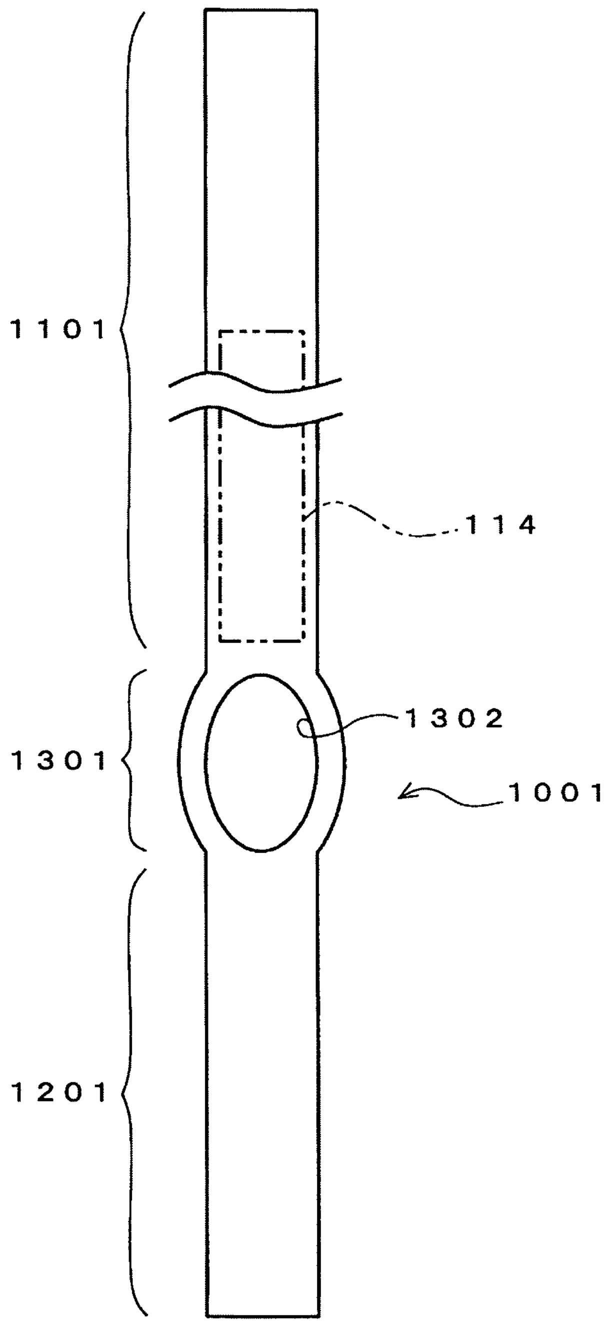
FIG. 9 is a plan view showing a belt according to a modified version.

A belt according to the modified version is shown in FIG. 9.

A belt 1001 in the modified version is generally identical in structure to the belt 100 in the first embodiment. There is no difference from the belt 100 in the first embodiment about how the belt is used.

A difference between this belt 1001 and the belt 100 in the first embodiment lies in that the belt 1001 is made as an integrated part in contrast to the belt 100 in the first embodiment in which the first band-shaped member 110 is connected to the second band-shaped member 120 through the joint member 130.

The belt 1001 does not have the joint member 130 which the belt 100 in the first embodiment has. Instead, it is like the first band-shaped member 110 connected directly in series to the second band-shaped member 120.

This belt 1001 comprises a first band-shaped portion 1101 that corresponds to the first band-shaped member 110 in the belt 100, a second band-shaped portion 1201 that corresponds to the second band-shaped member 120 in the belt 100, a connecting portion 1301 that corresponds to the joint member 130 in the belt 100. The connecting portion 1301 has an opening 1302 into which the first band-shaped portion 1101 can be inserted.

In the belt 1001, the first band-shaped portion 1101 is identical in structure to the first band-shaped member 110 in the belt 100, and the second band-shaped portion 1201 is identical in structure to the second band-shaped member 120 in the belt 100. The first band-shaped portion 1101 has the outer surface that is made of a thick fabric and the inner surface that is made of a thin fabric, as in the case in the first embodiment. The second band-shaped portion 1201 has the outer surface that is made of a thick fabric and the inner surface that is made of a thin fabric, as in the case in the first embodiment. Unlike the joint member 130 in the first embodiment, the connecting portion 1301 of the belt 1001 in the modified version has the outer surface that is made of a thick fabric and the inner surface that is made of a thin fabric, as in the case of the first band-shaped member 110 and the second band-shaped member 120.

In the belt 1001 in the modified version, a single piece of the thick fabric is used for the first band-shaped portion 1101, the second band-shaped portion 1201, and the connecting portion 1301. Likewise, a single piece of the thin fabric is used for the first band-shaped portion 1101, the second band-shaped portion 1201, and the connecting portion 1301.

A part of the first band-shaped portion 1101 that is closer to the connecting portion 1301 is made into a tube-like shape into which the inflatable pneumatic bag 114 is mounted, as in the belt 100 in the first embodiment. In addition, a second hook-and-loop fastener is provided on the inner surface of the first band-shaped portion 1101 at the end thereof, and a third hook-and-loop fastener is provided on the inner surface of the second band-shaped portion 1201 at the end thereof, as in the case of the belt 100 in the first embodiment.

Second Embodiment

Figure 10:
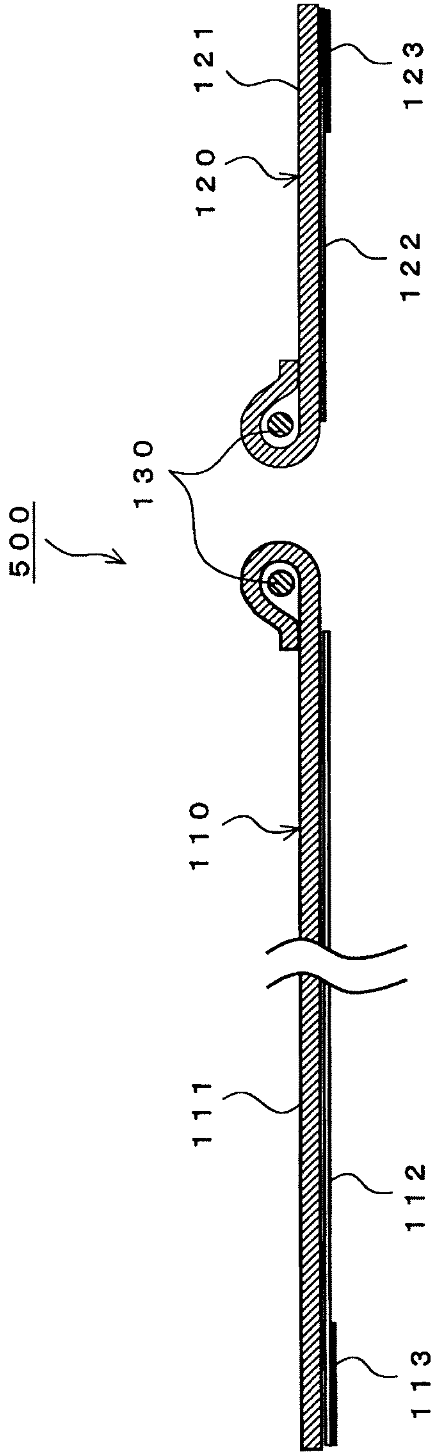
FIG. 10 is a cross-sectional view showing a configuration of a belt for KAATSU muscle training according to a second embodiment.
Figure 11:
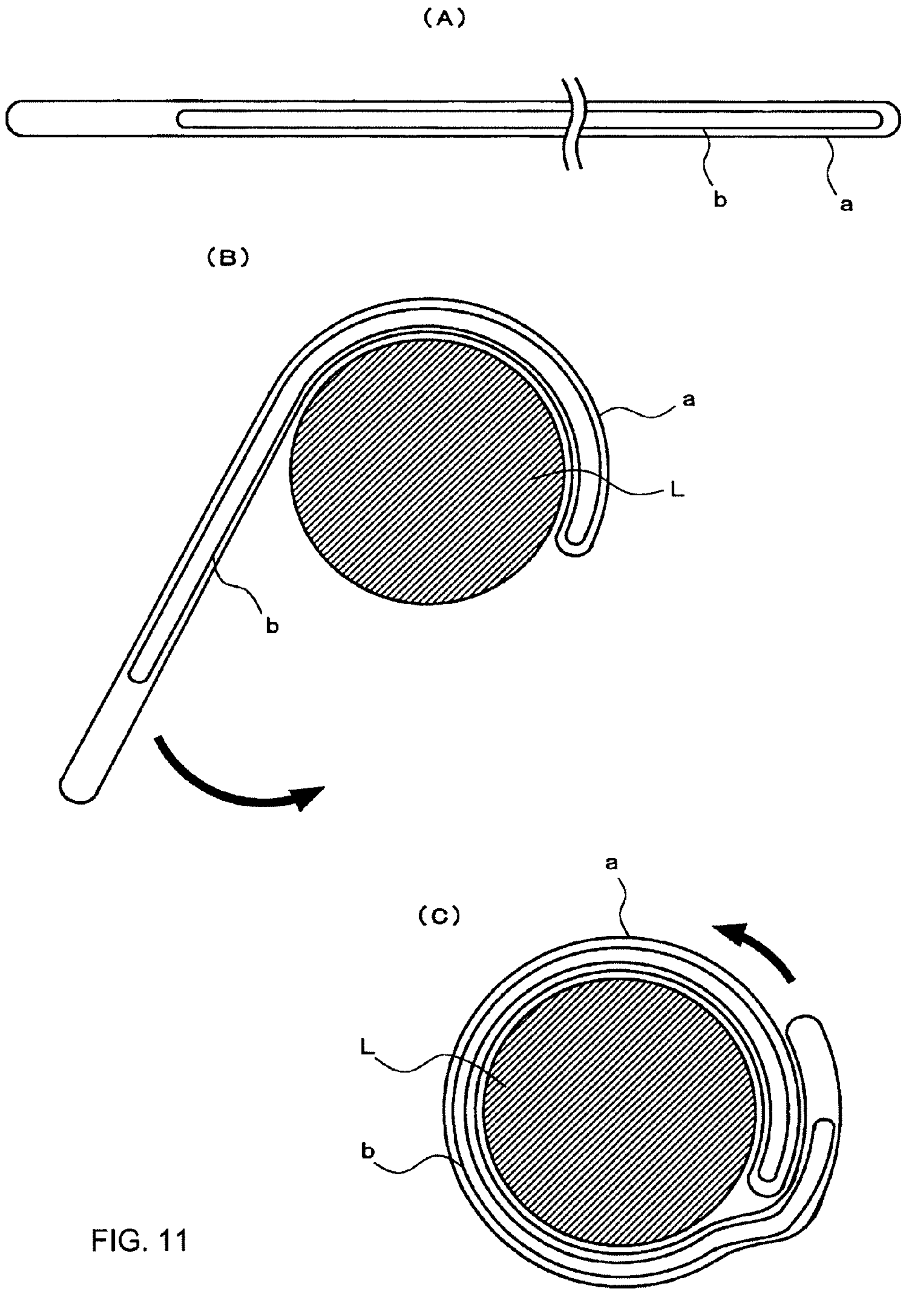
FIG. 11 is a view illustrating how a conventional belt for KAATSU muscle training is placed on a target compressed site.
Figure 12:
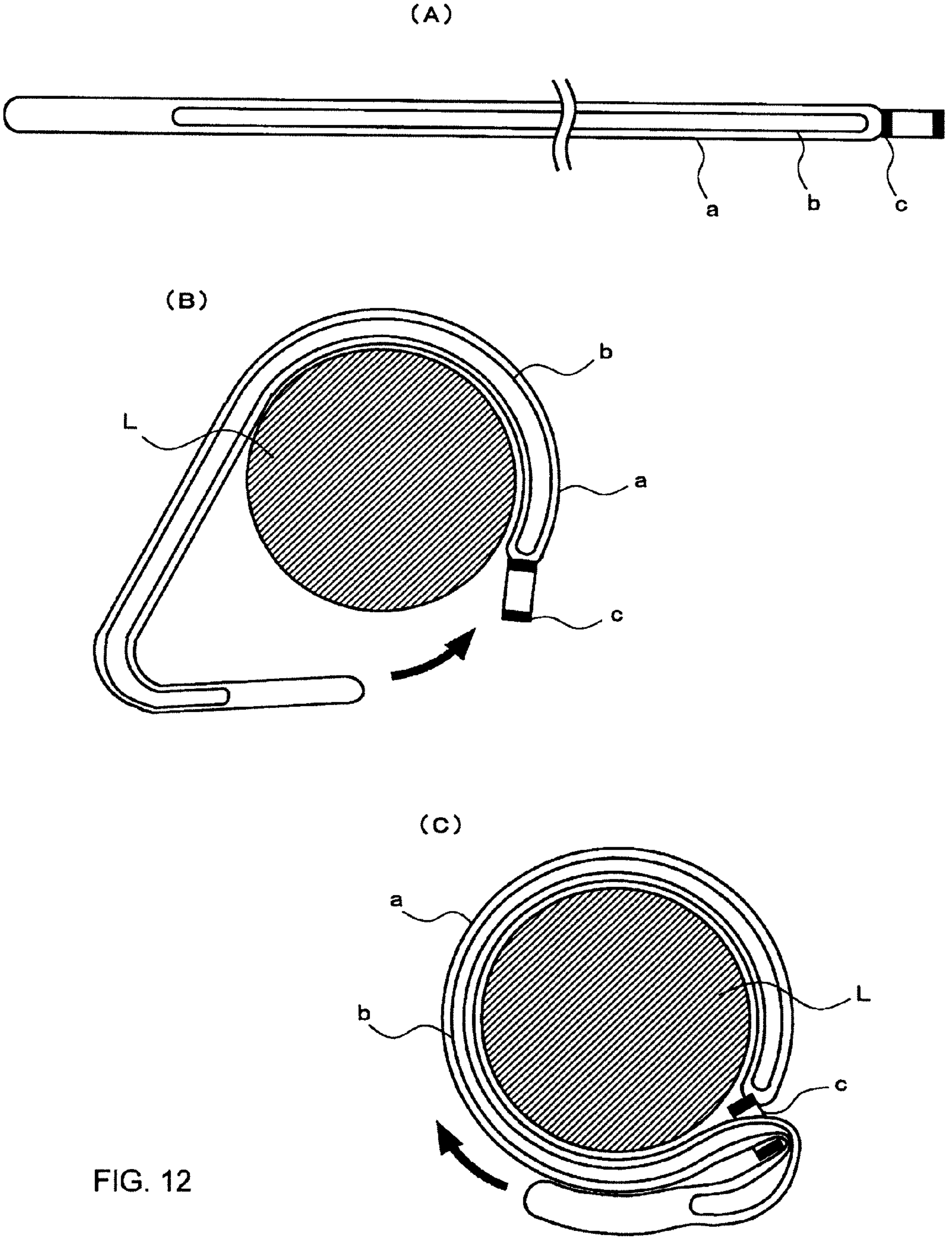
FIG. 12 is a view illustrating how another conventional belt for KAATSU muscle training is placed on a target compressed site.

A belt 500 for the KAATSU muscle training in a second embodiment is shown in FIG. 10.

In short, the belt 500 in the second embodiment is equivalent to the belt 100 in the first embodiment except that there is no inflatable pneumatic bag 114. Accordingly, the belt 500 in the second embodiment is not intended to be combined with the main device 200.

The belt 500 in the second embodiment has no inflatable pneumatic bag, so that there is no air pressure of the inflatable pneumatic bag that can be used for changing the compression force to be applied to the target compressed site by the belt 500.

The belt 500 in the second embodiment is different from the belt 100 in the first embodiment only in the structure of the first band-shaped member 110, as shown in FIG. 10. The first band-shaped member 110 of the belt 500 has the thick fabric 111 and the thin fabric 112, as in the case of first band-shaped member 110 in the first embodiment, but they are joined to each other by means of stitching for example. The first band-shaped member 110 of the belt 500 in the second embodiment has no tube-like portion and no inflatable pneumatic bag within the tube-like portion.

The belt 500 in the second embodiment is to be placed on a target compressed site of an arm or leg of a user by using similar procedures to those described in conjunction with the belt 100 in the first embodiment.

In this state, the user may be placed at rest. Alternatively, he or she can perform the KAATSU muscle training under the restriction of blood flow through the arm or leg on which the belt 500 is placed, by means of doing exercises though light.

The invention claimed is:

1. A belt for muscle training for the development of muscles that is used for applying a predetermined force for pressurization to a target compressed site near the proximal portion of one of the limbs of a user so that blood flow through the limb is restricted, the belt comprising:

a band-shaped member having a band shape;

and fastening means, wherein said fastening means is comprised of: a first hook-and-loop fastener that is provided on the outer surface of said band-shaped member at a position where said loop is to be formed; a second hook-and-loop fastener that is provided on the inner surface of said band-shaped member over a predetermined range from said one end of said band-shaped member, the second hook-and-loop fastener being adapted to be removably attached to said first hook-and-loop fastener; and a third hook-and-loop fastener that is provided on the inner surface of said band-shaped member over a predetermined range from said other end of said band-shaped member, the third hook-and-loop fastener being adapted to be removably attached to said first hook-and-loop faster, wherein an opening is formed between a one end of said band-shaped member and an other end thereof at a position closer to said other end such that a portion of said band-shaped member having a predetermined length from said one end can be inserted into the opening, wherein the length of said band-shaped member from said one end to said opening is equal to or longer than the length that is enough to be wound around said target compressed site one complete turn, the length of said band-shaped member from said other end to said opening is shorter than the length that is enough to be wound around said target compressed site one complete turn, and the total length of the band-shaped member is slightly shorter than twice the circumference of the target compressed site such that the one end of the band-shaped member is not overlapped with the other end thereof when the first hook-and-loop fastener and the second hook-and-loop fastener are engaged with each other, and the first hook-and-loop fastener and the third hook-and-loop fastener are engaged with each other, wherein a predetermined tension is applied to said band-shaped member by means of pulling said one end of said band-shaped member and said other end thereof in opposite directions, with said target compressed site of the user being placed in a loop made of a part of said band-shaped member extending from said opening to an appropriate position on the side of said one end, the loop being generated by means of passing said one end of said band-shaped member through said opening, and wherein the shape of said band-shaped member to which the predetermined tension is being applied is kept by means of said fastening means.

2. The belt for muscle training as claimed in claim 1, wherein said band-shaped member comprises:

a first band-shaped member extending from said one end of said band-shaped member to the opening;

a second band-shaped member extending from said other end of said band-shaped member to said opening; and a joint member that is connected to said first band-shaped member and said second band-shaped member, the joint member having an opening into which a portion of said first band-shaped member having a predetermined length from said one end can be inserted.

3. The belt for muscle training as claimed in claim 1, wherein an air-tight inflatable pneumatic bag is provided along a predetermined range from said opening on the portion of said band-shaped member from said one end to said opening, the length of the inflatable pneumatic bag being equal to or longer than the length that is enough to be wound around said target compressed site one complete turn, the inflatable pneumatic bag being adapted to supply gas from the outside to the inside thereof and to remove the gas within it from the outside.

4. The belt for muscle training as claimed in claim 2, wherein an air-tight inflatable pneumatic bag is provided, the length of the inflatable pneumatic bag being equal to or longer than the length that is enough to be wound around said target compressed site one complete turn, the inflatable pneumatic bag extending along a predetermined range from the proximal portion of said first band-shaped member where said first band-shaped member is connected to said joint member, the inflatable pneumatic bag being adapted to supply gas from the outside to the inside thereof and to remove the gas within it from the outside.

5. The belt for muscle training as claimed in claim 4, wherein said first band-shaped member has a hollow tube-like shape and said inflatable pneumatic bag is housed in said first band-shaped member.

6. The belt for muscle training as claimed in claim 1, wherein said fastening means comprises a fourth hook-and-loop fastener that is provided on the outer surface of said band-shaped member over a predetermined range from said other end of said band-shaped member to said opening, the fourth hook-and-loop fastener being adapted to be removably attached to said second hook-and-loop fastener.

7. The belt for muscle training as claimed in claim 1, wherein said band-shaped member is stretchable in the longitudinal direction thereof.

8. The belt for muscle training as claimed in claim 2, wherein said joint member has a ring shape.

9. The belt for muscle training as claimed in claim 3, wherein said inflatable pneumatic bag is stretchable in the longitudinal direction thereof.

* * * * *